US012220536B2

(12) United States Patent
Millar et al.

(10) Patent No.: US 12,220,536 B2
(45) Date of Patent: Feb. 11, 2025

(54) COMBINATION CPAP AND RESUSCITATION SYSTEMS AND METHODS

(71) Applicant: Fisher & Paykel Healthcare Limited, Auckland (NZ)

(72) Inventors: Gavin Walsh Millar, Auckland (NZ); Christopher Leigh Beaumont, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 111 days.

(21) Appl. No.: 17/858,892

(22) Filed: Jul. 6, 2022

(65) Prior Publication Data

US 2023/0125539 A1 Apr. 27, 2023

Related U.S. Application Data

(63) Continuation of application No. 15/973,262, filed on May 7, 2018, now Pat. No. 11,413,421, which is a
(Continued)

(51) Int. Cl.
*A61M 16/16* (2006.01)
*A61M 16/00* (2006.01)
(Continued)

(52) U.S. Cl.
CPC ........ *A61M 16/16* (2013.01); *A61M 16/0003* (2014.02); *A61M 16/024* (2017.08);
(Continued)

(58) Field of Classification Search
CPC .............. A61M 16/00; A61M 16/0057; A61M 16/0066; A61M 16/0069; A61M 16/06;
(Continued)

(56) References Cited

U.S. PATENT DOCUMENTS 2,893,381 A * 7/1959 Black .................. A61M 16/201
137/102
3,957,047 A * 5/1976 Freytag ................. A61M 16/00
128/204.24
(Continued)

FOREIGN PATENT DOCUMENTS

CA 2767070 1/2011
CN 201194980 2/2009
(Continued)

*Primary Examiner* — Joseph D. Boecker
(74) *Attorney, Agent, or Firm* — Knobbe, Martens, Olson & Bear, LLP

(57) ABSTRACT

A combination positive airway pressure (PAP) or continuous positive airway pressure (CPAP) and resuscitation system and related methods. The systems can be well-suited for use in providing CPAP therapy for a neonate or infant patient, with the ability to also provide resuscitation therapy at a peak inspiratory pressure (PIP) as needed or desired without switching to another system or switching the patient interface. The system can include an expiratory pressure device capable of regulating a positive end expiration pressure (PEEP) of the system, which preferably can also induce pressure oscillations relative to a mean PEEP.

30 Claims, 5 Drawing Sheets

Related U.S. Application Data continuation of application No. 14/391,864, filed as application No. PCT/NZ2013/000062 on Apr. 10, 2013, now Pat. No. 9,999,742.

(60) Provisional application No. 61/622,483, filed on Apr. 10, 2012.

(51) Int. Cl.

| | | |
|---|---|---|
| *A61M 16/04* | (2006.01) | |
| *A61M 16/06* | (2006.01) | |
| *A61M 16/08* | (2006.01) | |
| *A61M 16/10* | (2006.01) | |
| *A61M 16/12* | (2006.01) | |
| *A61M 16/20* | (2006.01) | |

(52) U.S. Cl.
CPC ........ *A61M 16/04* (2013.01); *A61M 16/0666* (2013.01); *A61M 16/105* (2013.01); *A61M 16/109* (2014.02); *A61M 16/201* (2014.02); *A61M 16/209* (2014.02); *A61M 16/0006* (2014.02); *A61M 2016/0027* (2013.01); *A61M 2016/003* (2013.01); *A61M 16/0066* (2013.01); *A61M 16/0069* (2014.02); *A61M 16/0841* (2014.02); *A61M 16/107* (2014.02); *A61M 16/1095* (2014.02); *A61M 16/125* (2014.02); *A61M 16/161* (2014.02); *A61M 16/162* (2013.01); *A61M 16/20* (2013.01); *A61M 16/204* (2014.02); *A61M 2205/3334* (2013.01); *A61M 2205/3348* (2013.01); *A61M 2205/3368* (2013.01); *A61M 2205/75* (2013.01); *A61M 2209/084* (2013.01); *A61M 2240/00* (2013.01)

(58) Field of Classification Search
CPC .......... A61M 16/0666; A61M 16/0841; A61M 16/0875; A61M 16/109; A61M 16/1095; A61M 16/16; A61M 16/20; A61M 16/201; A61M 16/202; A61M 16/203; A61M 16/204; A61M 16/205; A61M 2240/00

See application file for complete search history.

(56) References Cited

U.S. PATENT DOCUMENTS

| | | | |
|---|---|---|---|
| 4,502,481 A * | 3/1985 | Christian | A61M 16/00 |
| | | | 128/205.24 |
| 4,552,142 A | 11/1985 | Hoffman et al. | |
| 4,592,349 A | 6/1986 | Bird | |
| 4,782,831 A | 11/1988 | Gallant | |
| 5,040,532 A | 8/1991 | Alfery | |
| 5,388,571 A | 2/1995 | Roberts et al. | |
| 5,862,802 A | 1/1999 | Bird | |
| 6,135,108 A | 10/2000 | Hoenig | |
| 6,805,120 B1 | 10/2004 | Jeffrey et al. | |
| 9,999,742 B2 | 6/2018 | Millar et al. | |
| 11,413,421 B2 | 8/2022 | Miller et al. | |
| 2003/0047185 A1 | 3/2003 | Olsen | |
| 2004/0040559 A1 * | 3/2004 | Moody | A61M 16/0463 |
| | | | 128/204.24 |
| 2005/0072470 A1 | 4/2005 | Jacobs et al. | |
| 2007/0186928 A1 | 8/2007 | Be'Eri | |
| 2007/0204922 A1 | 9/2007 | Owczarczak | |
| 2008/0310994 A1 | 12/2008 | O'Donnell et al. | |
| 2010/0206310 A1 * | 8/2010 | Matsubara | A61M 16/209 |
| | | | 128/205.24 |
| 2010/0263669 A1 | 10/2010 | Bowsher | |
| 2011/0073112 A1 * | 3/2011 | DiBlasi | A61M 16/0006 |
| | | | 128/205.24 |
| 2011/0079222 A1 | 4/2011 | DiBlasi et al. | |
| 2012/0085348 A1 * | 4/2012 | Chalvignac | H02K 7/14 |
| | | | 128/205.24 |
| 2013/0220326 A1 * | 8/2013 | Kemps | A61M 16/20 |
| | | | 128/205.23 |
| 2013/0263851 A1 * | 10/2013 | Arcilla | A61M 16/1075 |
| | | | 128/203.14 |
| 2014/0283831 A1 | 9/2014 | Foote et al. | |
| 2015/0075524 A1 | 3/2015 | Millar et al. | |
| 2018/0311461 A1 | 11/2018 | Millar et al. | |

FOREIGN PATENT DOCUMENTS

| | | |
|---|---|---|
| CN | 202020765 | 11/2011 |
| WO | WO 2002/013898 A2 | 2/2002 |
| WO | WO 2007/19625 A1 | 2/2007 |
| WO | WO 2012/108826 A1 | 8/2012 |

* cited by examiner

COMBINATION CPAP AND RESUSCITATION SYSTEMS AND METHODS

INCORPORATION BY REFERENCE TO ANY PRIORITY APPLICATIONS

Any and all applications for which a foreign or domestic priority claim is identified in the Application Data Sheet as filed with the present application are hereby incorporated by reference in their entireties and made a part of the present disclosure.

BACKGROUND

Field of the Invention

The present invention relates to breathing assistance systems and methods. In particular, the present invention relates to systems and methods for providing positive airway pressure therapy or resuscitation therapy to an infant.

Description of the Related Art

Under certain circumstances it is necessary or desirable to provide breathing assistance to a patient under respiratory distress. For example, breathing assistance is often a necessary therapy to treat respiratory distress syndrome (RDS) in infants, which can also be referred to as neonatal respiratory distress syndrome or respiratory distress syndrome of newborn. The breathing assistance provided is often in the form of providing breathing gases at a positive pressure, or a pressure somewhat greater than atmospheric pressure. Such treatments may be referred to in general as positive airway pressure (PAP) therapy. Often, the positive pressure is provided by a continuous flow of breathing gases, which is referred to as continuous positive airway pressure (CPAP) therapy. Infants on CPAP therapy to treat respiratory distress syndrome may also be likely to stop breathing and require resuscitation therapy.

SUMMARY

A preferred embodiment is a combination positive airway pressure and resuscitation system and, preferably, a continuous positive airway pressure and resuscitation system, as well as methods relating to the set-up and use of such a system. Conventionally, in response to RDS, an infant is treated with a PAP system for an extended period of time. If necessary, a separate resuscitation system is utilized to provide resuscitation. Subsequently, the use of the PAP system is resumed. This method results in inefficiencies caused by the switchover from one system to the other. In particular, the patient interface is usually switched when going from one system to the other, which can be time consuming and disruptive to the infant. The preferred systems and methods allow PAP or CPAP therapy for extended periods, along with intermittent resuscitation, in a quick and efficient manner and without requiring the patient interface to be changed.

A preferred embodiment involves a combination infant positive airway pressure and resuscitation system, including an integrated inspiratory pressure device comprising a resuscitator and a humidifier. The resuscitator is capable of regulating a flow of breathing gas to a desired peak inspiration pressure. The humidifier humidifies the flow of breathing gas. An expiratory pressure device is configured to receive expiratory gases from an expiratory circuit and regulate the expiratory gases to a positive end expiration pressure. An occlusion device is within the expiratory circuit upstream from the expiratory pressure device and is configured to permit occlusion of the expiratory circuit at desired times such that the pressure within the inspiratory circuit rises to the peak inspiration pressure of the resuscitator.

In some embodiments of the above-described system, the resuscitator is separable from the humidifier. The resuscitator can be integrated with a first housing and the humidifier can be integrated with a second housing. Some of the above-described system can include a flow generator that generates the flow of breathing gas. The flow generator can be integrated with the second housing.

A preferred embodiment involves a combination infant positive airway pressure and resuscitation system. The system includes an inspiratory pressure device that outputs a flow of breathing gas at a desired peak inspiration pressure to an inspiratory circuit. A patient interface receives the flow of breathing gas from the inspiratory circuit, wherein the patient interface is configured to deliver the flow of breathing gas to an infant patient and receive expiratory gases from the patient. An expiratory circuit receives the expiratory gases from the patient interface. An expiratory pressure device receives expiratory gases from the expiratory circuit and regulates the expiratory gases to a positive end expiration pressure. An occlusion device is positioned within the expiratory circuit upstream from the expiratory pressure device. The occlusion device is configured to permit occlusion of the expiratory circuit at desired times such that the pressure within the inspiratory circuit rises to the peak inspiration pressure.

Another preferred embodiment involves a combination infant positive airway pressure and resuscitation system. The system includes a supply of breathing gas and an inspiratory pressure device that receives a flow of breathing gas from the supply of breathing gas. The inspiratory pressure device is capable of outputting the flow of breathing gas at a desired peak inspiration pressure to an inspiratory circuit. A patient interface receives the flow of breathing gas from the inspiratory circuit, wherein the patient interface is configured to deliver the flow of breathing gas to an infant patient and receive expiratory gases from the patient. An expiratory circuit receives the expiratory gases from the patient interface. An oscillatory expiratory pressure device receives expiratory gases from the expiratory circuit and regulates the expiratory gases to a mean positive end expiration pressure with pressure oscillations relative to the mean pressure. An occlusion device is positioned within the expiratory circuit and is configured to permit occlusion of the expiratory circuit at desired times such that the pressure within the inspiratory circuit rises to the peak inspiration pressure.

In some arrangements of the above-described systems, the expiratory pressure device is or includes a water resistance valve, which can be adjustable to permit adjustment of the positive end expiration pressure. The occlusion device can be a manual push button valve or a clamp valve, among other possible valve types. In some arrangements, the system can include a humidifier positioned within the inspiratory circuit between the inspiratory pressure device and the patient interface. Preferably, the occlusion device is located less than 500 millimeters from the patient end of the expiratory circuit. In some arrangements, the expiratory circuit can include an expiratory hose coupled to the patient interface and the occlusion device can be located within the expiratory hose.

In some arrangements, a source of breathing gas is provided separately from the inspiratory pressure device, such as via a bottle or wall source. In other arrangements, the source of breathing gas is ambient air and a flow of air is generated by a flow generator or blower. The blower can be provided in an integrated unit with the inspiratory pressure device (e.g., resuscitator) and the humidifier. In some arrangements, the blower and humidifier are contained or associated with a first housing and the inspiratory pressure device (e.g., resuscitator) can be integrated with a second housing, which can be removed from the first housing. In some arrangements, the humidifier is contained or associated with a first housing and the inspiratory pressure device (e.g., resuscitator) can be integrated with a second housing, which can be removed from the first housing. In some arrangements, the blower can be integrated with the humidifier and the inspiratory pressure device (e.g., resuscitator) can be a separate component.

Another preferred embodiment involves a combination infant positive airway pressure and resuscitation system. The system includes a patient interface that receives expiratory gases from the patient and an expiratory circuit that receives the expiratory gases from the patient interface. An expiratory pressure device receives expiratory gases from the expiratory circuit and regulates the expiratory gases to a positive end expiration pressure. An occlusion device is positioned within the expiratory circuit upstream from the expiratory pressure device and is configured to permit occlusion of the expiratory circuit at desired times such that the pressure within the system rises above the positive end expiration pressure.

A preferred embodiment involves a breathing circuit for a combination infant positive airway pressure and resuscitation system. The circuit includes an expiratory circuit that is configured for connection to a patient interface to receive expiratory gases from the patient interface and an inspiratory circuit that is configured for connection to the patient interface to deliver a flow of breathing gas to the patient interface. An occlusion device is configured to permit occlusion of the expiratory circuit at desired times such that the pressure within the system rises above the positive end expiration pressure.

In some arrangements of the above-described circuits, the expiratory circuit is further configured for connection to an expiratory pressure device that receives expiratory gases from the expiratory circuit and regulates the expiratory gases to a positive end expiration pressure. The occlusion device can comprise a manual push button valve. The occlusion device can comprise a clamp. The occlusion device can be located less than 500 millimeters from the patient interface along the expiratory circuit. The occlusion device can be located in the expiratory circuit. In some embodiments, the occlusion device can be located in the patient interface.

Another preferred embodiment involves a method of providing continuous positive airway pressure and resuscitation to an infant, including using an inspiratory pressure device to provide a flow of breathing gas, the inspiratory pressure device capable of generating a peak inspiratory pressure in the flow of breathing gas. The flow of breathing gas is supplied to an infant patient through a patient interface and expiratory gases are received from the infant patient through the patient interface. A water resistance valve or other type of oscillatory resistance valve is utilized to vent the flow of breathing gas and expiratory gases and maintain a mean positive end expiration pressure within the patient interface that is less than the peak inspiratory pressure. A resuscitation breath is provided to the infant patient by blocking the flow of breathing gas and expiratory gases between the patient interface and the water resistance valve such that the pressure within the patient interface increases to the peak inspiratory pressure.

In some applications, the method can include providing repeated resuscitation breaths to the infant patient by repeatedly alternating between blocking and allowing the flow of breathing gas and expiratory gases between the patient interface and the water resistance valve. In some applications, the blocking of the flow of breathing gas and expiratory gases between the patient interface and the water resistance valve can be accomplished by actuating a push button occlusion valve or by clamping a portion of an expiratory tube. In some applications, the flow of breathing gas can be passed through a humidifier after the inspiratory pressure device and before the patient interface. The positive end expiration pressure can be adjusted by adjusting a depth of an outlet of the flow of breathing gas and expiratory gases within a water reservoir of the water resistance valve.

BRIEF DESCRIPTION OF THE DRAWINGS

Preferred embodiments, having certain features, aspects and advantages of the present invention, are described with reference to the accompanying drawings. The drawings contain six (6) figures.

FIG. 3A shows the tube in an open configuration and FIG. 3B shows the tube in a collapsed or occluded configuration.

DETAILED DESCRIPTION

Figure 1A:
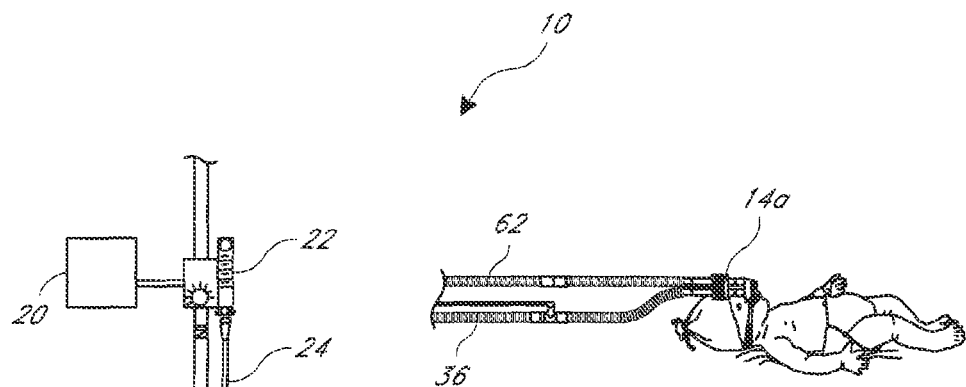
FIG. 1A is an illustration of an infant patient and an alternative patient interface.
Figure 1:
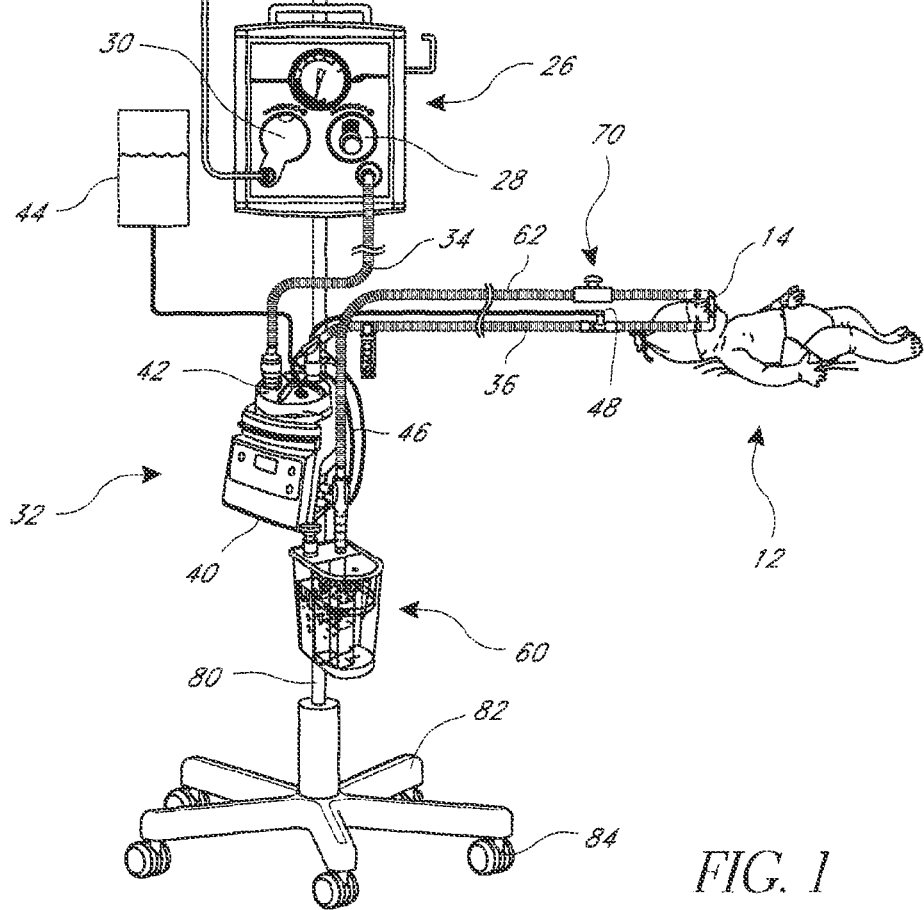
FIG. 1 is an illustration of an infant patient receiving CPAP therapy and/or resuscitation therapy from a system including an inspiratory pressure device, a humidifier, a patient interface and an expiratory pressure device.

FIG. 1 illustrates a combination infant positive airway pressure (PAP) or continuous positive airway pressure (CPAP) and resuscitation system, generally referred to by the reference numeral 10. The system 10 is capable of providing PAP or CPAP therapy to a neonate or an infant patient 12 for an extended period of time, while also permitting resuscitation breaths to be delivered to the infant patient 12 if or when necessary. Preferably, both the PAP or CPAP therapy and the resuscitation breaths are delivered through a single patient interface 14 without requiring removal of the interface 14 from the infant patient 12. The present system 10 is disclosed herein in the context of continuous positive airway pressure (CPAP) therapy; however, the system 10 could also provide other types or modes of positive airway pressure (PAP) therapy. Accordingly, references to CPAP therapy herein are understood to also include other types of PAP therapies, unless specifically noted otherwise.

The illustrated system 10 includes a source of breathing gas 20, which can be a gas cylinder (not shown), a wall supply 20, or any other suitable source of breathing gas. The breathing gas can be air, oxygen, a blend of air and oxygen, or any other suitable gas for use in respiratory therapy. The source of breathing gas 20 provides a flow of breathing gas at an initial feed pressure or within an initial feed pressure range. The flow rate of the flow of breathing gas can be adjusted by a suitable flow meter or gas blender 22 to a suitable level for the desired therapy.

A suitable conduit, such as a gas supply line 24 supplies the flow of breathing gas to an inspiratory pressure device 26, which can be a resuscitator. More preferably, the inspiratory pressure device 26 is an infant resuscitator, such as an infant resuscitator sold by Fisher and Paykel Healthcare, the Assignee of the present application, under the NEOPUFF trademark. Although referred to herein as a "resuscitator" for convenience, it is understood that the term can encompass other suitable types of inspiratory pressure devices capable of providing a breathing gas at a controlled output pressure.

Preferably, the resuscitator 26 is capable of receiving a flow of breathing gas from the source of breathing gas 20 and outputting the flow of breathing gas at a controlled pressure greater than atmospheric pressure. In particular, the resuscitator 26 can output the flow of breathing gas at a peak inspiratory pressure (PIP), which preferably can be up to about 75 cmH$_2$O or greater. Preferably, the resuscitator 26 includes an adjustment mechanism, such as an adjustment valve 28, which allows the PIP to be adjusted to a desired pressure level. Preferably, the resuscitator 26 also incorporates a pressure relief valve 30 that regulates a maximum pressure within the system 10. The pressure relief valve 30 can be adjustable such that the maximum system pressure can be adjusted. For example, an adjustment range can be between about 5-70 cmH$_2$O. The pressure relief level can be factory set to a particular value, such as about 40 cmH$_2$O, for example. However, in alternative arrangements, a separate pressure regulator could be provided within the system 10 to regulate the maximum system pressure. Such a pressure regulator is described in U.S. Pat. No. 6,644,313, which is incorporated by reference herein in its entirety. In embodiments having a blower unit, a pressure relief valve may not be necessary because the maximum achievable pressure of the system can be regulated by the blower unit. The blower unit can be designed so that the maximum pressure it can produce is lower than a desired pressure relief level. In other embodiments, the maximum achievable pressure of the blower unit can be limited by software in the system.

The flow of breathing gas outputted from the resuscitator 26 preferably is delivered to an optional humidifier system 32 by a suitable conduit, such as an inspiratory tube or supply tube 34. In some embodiments, the resuscitator and the humidifier system can be integrated into a single unit, as discussed below. The humidifier system 32 provides humidity or vaporized liquid, such as water, to the flow of breathing gas received from the resuscitator 26 to output a flow of humidified breathing gas to the patient interface 14 through a suitable conduit, such as a supply tube 36. The humidifier system 32 can include a humidifier unit or humidifier 40 and a humidity chamber 42. The humidity chamber 42 holds a volume of liquid, such as water, which is heated by the humidifier 40 to create a vapor within the humidity chamber 42 that is transferred to the flow of breathing gas. The humidity chamber 42 can be an auto-fill variety, in which a source of liquid 44 is connected to the humidity chamber 42 to refill the volume of liquid, as appropriate. A suitable humidifier 40 is the MR850 Humidifier sold by the Assignee of the present application. A suitable humidity chamber 42 is the MR225 or MR290 humidity chamber sold by the Assignee of the present application. The humidifier system 32 can output a flow of humidified breathing gas at a desired temperature and absolute humidity, such as an optimal temperature of about 37 degrees Celsius and absolute humidity of about 44 mg/L, or within a desirable or acceptable range of the optimal temperature and absolute humidity.

The supply tube 36 can be a heated supply tube such that a temperature of the flow of breathing gas is maintained at an elevated level within the supply tube 36 and to avoid or limit condensation within the supply tube 36 or patient interface 14. A heating element cable 46 can connect a heating element of the supply tube 36 to the humidifier 40 (or other power/heat source) to power the heating element. A sensor or probe 48 can be coupled to the humidifier 40 and supply tube 36 to detect the temperature and/or flow rate of the flow of breathing gas through the supply tube 36. Preferably, the sensor 48 is spaced from the inlet end of the supply tube 36 and can be located at the outlet end of the supply tube 36. The sensor 48 can include a wire that couples the sensor 48 to the humidifier 40. The humidifier 40 can utilize information from the sensor 48 to control the operating parameters of the humidifier 40, for example, to maintain the temperature and/or humidity of the flow of breathing gas within the supply tube 36 at a desirable level or range.

From the humidifier system 32, the flow of breathing gas is supplied to the patient interface 14, which can be any suitable type of interface capable of supplying a breathing gas to the respiratory system of the patient. The illustrated interface 14 is a lateral nasal interface, which includes nasal cannula or nasal prongs that are inserted into the nostrils of the infant patient 12. In a lateral interface, the inlet and outlet are laterally spaced on opposing sides of the nasal cannula or prongs and a midline of the infant patient 12. FIG. 1A illustrates an alternative nasal interface 14A, which can be referred to as a midline nasal interface. The midline nasal interface 14A positions the inlet and the outlet of the interface 14A are located in line with the nasal cannula or nasal prongs and substantially along the midline of the infant patient 12. The inlet and outlet of the interface 14A can be positioned side-by-side; however, in a preferred arrangement, the inlet and outlet are stacked one on top of the other. One suitable interface 14A is an infant nasal tube or mask in combination with nasal prongs sold by the Assignee of the present application under the trademark FLEXITRUNK. However, other suitable patient interfaces 14 can also be used, such as a face mask that covers both the nose and mouth of the infant patient 12 (e.g., RD Series Infant Resuscitation Masks sold by the Assignee of the present application) or an appropriate interface device in combination with an endotracheal tube. An infant resuscitation mask is described in U.S. Pat. No. 7,341,059, which is hereby incorporated by reference in its entirety.

Preferred interfaces 14 provide a sealed system that delivers the flow of breathing gas to the infant patient 12 and receives expiratory gases from the patient 12. Preferably, the system 10 is a biased flow system in which breathing gas is constantly flowing within the system 10 generally in a direction from the inlet of the patient interface 14 to the outlet of the patient interface 14. Thus, the infant patient 12 can inhale a portion of the flow of breathing gas and the remainder is passed through the patient interface 14. Exhaled or expiratory gases can mix with the flow of breathing gas and exit the patent interface 14 along with the unused portion of the flow of breathing gas. For convenience, the gases exiting the patient interface 14 are referred to as expiratory gases or the flow of breathing gas, although it is understood that either or both of patient exhaled gases and unused breathing gases can be present at any particular point in time.

Expiratory gases flow from the patient interface 14 to an expiratory pressure device 60, which is configured to regulate the minimum pressure within the system 10, preferably to a level above ambient or atmospheric pressure. Preferably, the expiratory pressure device 60 is connected to the patient interface 14 by a suitable conduit, such as an expiratory hose 62. However, in an alternative arrangement, the expiratory pressure device 60 can be connected directly to or integrated with the patient interface 14.

Preferably, the expiratory pressure device 60 is configured to provide a minimum pressure or minimum backpressure within the system 10 and, in particular, at the patient interface 14, which can be referred to as the positive end expiration pressure (PEEP). In the illustrated system 10, the PEEP is equivalent to, or generally equivalent to, the continuous positive airway pressure (CPAP). Accordingly, such a device can be referred to as a CPAP generator. However, preferably, the expiratory pressure device 60 is an oscillatory valve capable of providing pressure oscillations relative to a mean PEEP pressure. It is believed that such pressure oscillations are beneficial to the infant patient 12 and may result in improved gas exchange and reduce the infant patient's 12 work of breathing. Thus, an oscillatory pressure expiratory pressure device 60 is particularly preferred. One type of oscillating pressure expiratory pressure device 60 is a fluid resistance valve, in particular a liquid or water resistance valve, which is often referred to as a bubbler. In general, a water resistance valve delivers the expiratory gases to an outlet that is submerged in a water reservoir resulting in a resistance to the exit of the expiratory gases that is greater than that caused by ambient or atmospheric pressure and related to the depth of the outlet relative to a surface of the water within the water reservoir. In some arrangements, the depth of the outlet is adjustable to allow the PEEP to be adjusted to a desired level. One suitable bubbler is the Bubble CPAP generator sold by the Assignee of the present application. Additional details of a suitable bubbler device are described in U.S. Pat. No. 6,805,120, which is incorporated by reference herein in its entirety. Preferably, the bubbler (or other oscillatory pressure device) is capable of producing vibrations in the infant patient's chest at a frequency of between about 5-30 Hz.

The illustrated system 10 also includes an occlusion device or occlusion valve 70 that is configured to selectively block the flow of gases within the system 10 and preferably block the flow of expiratory gases, such as within the patient interface 14, expiratory tube 62 or expiratory pressure device 60. Preferably, the occlusion valve 70 is located upstream of the expiratory pressure device 60 and downstream of the patient interface 14, such as within the expiratory tube 62. Preferably, the occlusion valve 70 is located at or near the patient interface 14, such as within about 500 millimeters or less of the patient interface 14. However, in other arrangements, the occlusion valve 70 can be integrated with the patient interface 14 or expiratory pressure device 60. The occlusion valve 70 is configured to block the exit of gases from the system 10 to a sufficient extent such that the gas pressure within the system 10 rises above the PEEP. With the exit of gases from the system 10 blocked, the inspiratory pressure device 26 can increase the pressure in the system 10 preferably to or near the set PIP level. The occlusion valve 70 can completely or substantially completely block the flow of gas within the system 10, or can block or interrupt the flow to a sufficient extent to allow the inspiratory pressure device 26 or integrated unit 90 to raise the pressure toward the PIP. Preferably, the occlusion valve 70 can block the flow of gas within the system 10 to a sufficient extent that the inspiratory pressure device 26 or integrated unit 90 can raise the pressure within the system 10 to or substantially to the PIP pressure. However, to quickly and accurately achieve the PIP pressure, it is desirable that the occlusion valve 70 completely or substantially completely block the flow of gas within the system 10. Although described as a sealed system, it is understood that some leakage of gas may occur from the system 10, such as between the patient interface 14 and the patient 12, for example. In addition, pressure losses may occur throughout the system 10 such that the pressure is not the same throughout the entire system 10. Accordingly, it is understood that the PEEP or PIP may vary between the point of measurement and some other point within the system 10. Therefore, it is understood that discussion of specific pressures or pressure ranges herein, such as PIP or PEEP, incorporates a range of acceptable variation, which can result from pressure leakage, pressure loss or measurement error.

In operation, the occlusion valve 70 can be utilized to perform a resuscitation procedure or resuscitation therapy by raising the pressure within the system 10 to at or near the PIP pressure to deliver a resuscitation breath to the infant patient 12 in a manner similar to a conventional resuscitation procedure. However, advantageously, with the present system 10, resuscitation breaths can be provided to an infant patient 12 that is undergoing CPAP therapy immediately and without requiring additional equipment or set-up. Furthermore, the CPAP therapy can be immediately resumed after the resuscitation procedure. Preferably, the resuscitation breaths can be provided through the same patient interface 14 as the CPAP therapy without removal or exchange of the interface and with breathing gases flowing in the same direction within the system 10 as the CPAP therapy. The occlusion valve 70 can be used to provide repeated resuscitation breaths to the infant patient 12 at or near PIP pressure with intervening periods of PEEP. The resuscitation breaths delivered by use of the occlusion valve 70 can be at any suitable rate, such as about 40-60 breaths per minute. The relative duration of the resuscitation breath time at PIP pressure to the exhalation time at PEEP can be any suitable ratio, such as 40:60, 50:50, 60:40, or any value in between. The resuscitation procedure typically lasts for less than 30 minutes or less than 15 minutes. Often, the resuscitation procedure lasts between about 3-5 minutes. Thus, the present system 10 is particularly advantageous in reducing the switchover time between CPAP therapy and resuscitation therapy, which avoids delay in providing resuscitation therapy once it is recognized as necessary or desirable.

The occlusion valve 70 can be of any suitable arrangement or structure to selectively accomplish a partial or complete occlusion of gas flow within the system 10. Preferably, the occlusion valve 70 allows the cycling between an occluded or closed position and an open position at a suitable rate, such as the rates described herein. In some arrangements, the occlusion valve 70 is a manual valve that is operated by manually by a caregiver. Accordingly, preferably the occlusion valve 70 facilitates repeated cycling between the open and closed position multiple times per minute.

Figure 2:
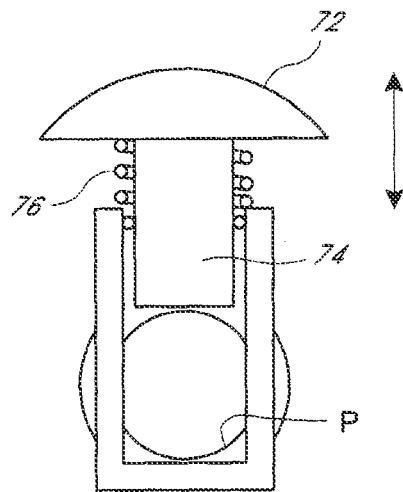
FIG. 2 is a partial cross-sectional view of a linear motion, push button occlusion valve.
Figure 3A:
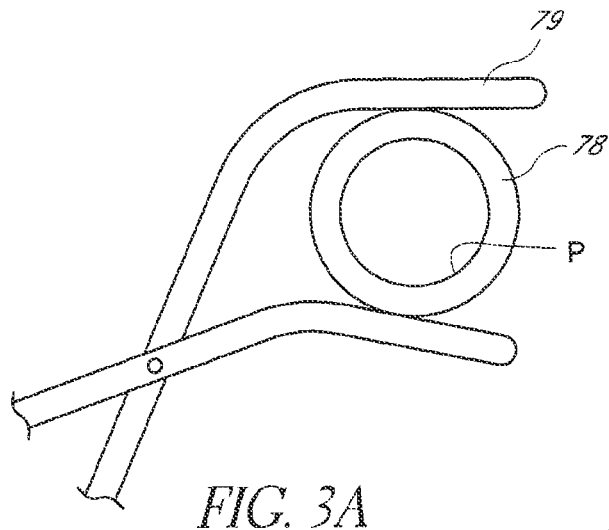
FIGS. 3A and 3B are partial cross-sectional views of a clamp-type occlusion valve in which a tube can be collapsed or occluded by a clamp.
Figure 3B:
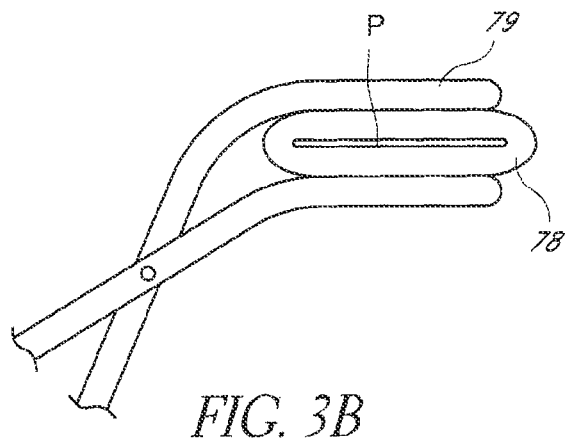

For example, FIG. 2 illustrates a push button valve arrangement 70 having a manually operated push button 72 that actuates a valve body 74 movable between an open position and a closed position. The valve body 74 can simply move into or out of a flow passage P of the system 10 (linear movement or translation) to selectively allow and occlude gas flow within the system 10. In some embodiments, the valve arrangement can include a safety feature to help prevent accidental actuation. For example, the push button may be lockable in the open position by rotating the push button a quarter turn. In order to use the valve arrangement, the user can rotate the push button to unlock before actuating. Preferably, the valve body 74 is biased to the open position by a biasing member, such as a spring 76, so that gas flow is normally unobstructed. The valve body 74 can be movable to the closed position (e.g., using the manual push button 72) when it is desired to deliver a resuscitation breath at PIP. In other arrangements, the valve 70 could be a rotatable valve, such as a stopcock. FIG. 3 illustrates another possible occlusion valve arrangement 70, in which a compliant section of tubing 78 that has sufficient resilience to remain open in the absence of an external force (FIG. 3A), but can be collapsed to a closed position in response to an external squeezing force (FIG. 3B), such as a force applied by a clamping mechanism 79. In still other arrangements, the valve 70 could be automatically movable (e.g., electronically actuated).

As described, the occlusion valve 70 can be positioned in any suitable location within the system 10. The system 10 can be considered to have an inspiratory circuit and an expiratory circuit. In the illustrated arrangement, the inspiratory circuit can include all or portions of the source of breathing gas 20, the gas supply line 24, the inspiratory pressure device 26, the supply tube 34, the humidifier system 32, and the supply tube 36. The expiratory circuit can include all or portions of the expiratory tube 62 and the expiratory pressure device 60. A portion of the patient interface 14 can be predominantly occupied by a flow of inspiratory breathing gas prior to inspiration by the infant patient 12 or prior to availability to the infant patient 12, while another portion of the patient interface 14 can be predominantly occupied by a flow of expiratory gas exhaled by the infant patient 12 or that has bypassed the infant patient 12. Accordingly, the patient interface 14 can be considered to form a part of each of the inspiratory circuit and the expiratory circuit. A portion of the patient interface 14 can also include a mixture of inspiratory gas and expiratory gas, at least for certain time durations, and may not be considered part of either of the inspiratory circuit or the expiratory circuit or may be considered as a part of each.

The various components of the system 10, including those described above, can be arranged and/or mounted in any suitable manner. Some or all of the components can be stationary (e.g., wall mounted) or movable. In the illustrated arrangement, some of the components are mounted to a support pole 80, which includes a base portion 82 having a plurality of rollers or casters 84 to provide mobility. A suitable pole 80 is the 900MR292 or 900MR293 pole sold by the Assignee of the present application. In the illustrated arrangement, the inspiratory pressure device 26, the humidifier system 32 and the expiratory pressure device 60 are mounted to the support pole 80. Although not specifically illustrated, the source of water 44 preferably is also supported by the support pole 80. In other arrangements, some of the components could be mounted on another support pole 80. The source of breathing gas 20 and the flow meter or gas blender 22 can be mobile or can be stationary (e.g., wall mounted). In one arrangement, for example, the resuscitator 26 can be integrated with an infant warmer, such as the 900 Series infant warmers sold by the Assignee of the present invention.

To set up the system 10 for use, the components can be gathered and mounted to the support pole 80 or other support structure, if necessary or desired. The components can be connected to a power source, if necessary, and turned on. The inspiratory pressure device 26 can be coupled to the source of breathing gas 20 through the flow meter or gas blender 22 by the gas supply line 24. The humidifier system 32 can be coupled to the inspiratory pressure device 26 by the supply tube 34. The source of water 44 can be coupled to the humidity chamber 42. The patient interface 14 can be coupled to the humidifier system 32 by the supply tube 36. The expiratory pressure device 60 can be coupled to the patient interface 14 by the expiratory tube 62. The occlusion valve 70 can be integrated into the expiratory tube 62; however, the occlusion valve 70 can also be assembled to the expiratory tube 62 (such as intermediate two tube portions of the expiratory tube 62) or otherwise assembled in a suitable location within the system 10, as described above.

If necessary, the expiratory pressure device 60 can be filled with a liquid, such as about 500 milliliters of water. If adjustable, the expiratory pressure device 60 can be initially adjusted to a maximum pressure level (maximum PEEP). The humidifier system 32 can be adjusted to a desired temperature and absolute humidity, such as about 37 degrees Celsius and 44 mg/L. The flow meter or gas blender 22 can be adjusted to a desired flow rate, preferably less than 15 liters per minute (LPM). In embodiments having a blower unit, the flow meter or gas blender can be integrated with the blower unit. More preferably, the flow rate is adjusted to between about 6-8 LPM.

If necessary or desirable, the pressure relief valve 30 of the inspiratory pressure device 26 can be adjusted to a suitable pressure relief level. The pressure relief valve 30 can be factory set to a pressure relief level, such as about 40 $cmH_2O$. The pressure relief valve 30 can be set to a lower level, such as between about 5-70 $cmH_2O$ and, more preferably, 30-40 $cmH_2O$. To set the level of the pressure relief valve 30, the PIP adjustment of the inspiratory pressure device 26 is adjusted to a maximum level. The patient interface 14 can be blocked or connected to a test lung apparatus, such as the RD020-01 test lung apparatus sold by the Assignee of the present application. The occlusion valve 70 can be actuated to allow the pressure within the system 10 to rise to the pressure relief level, which can be adjusted to a desired level. With the occlusion valve 70 still actuated, the PIP can be adjusted to a desirable level, preferably less than about 75 $cmH_2O$. More preferably, the PIP is between about 10-40 $cmH_2O$ or 20-30 $cmH_2O$. In one application, the PIP pressure is adjusted to about 20 $cmH_2O$, using the PIP valve 28. The occlusion valve 70 can be moved to an open position such that the system pressure is reduced to the PEEP value as determined by the expiratory pressure device 60. The PEEP level can be adjusted to a desirable pressure, such as less than about 25 $cmH_2O$, by adjusting a depth of the gas outlet within the water reservoir. Preferably, the PEEP level is adjusted to less than about 15 $cmH_2O$, less than about 9 $cmH_2O$ or less than about 5 $cmH_2O$. In one application, the PEEP level is set to about 5 $cmH_2O$. If necessary, the test lung apparatus can be removed and the system 10 is ready for use.

To use the system 10, the patient interface 14 can be applied to an infant patient 12 following an appropriate methodology. For example, a face mask can be positioned over the nose and mouth of the infant patient 12 and, if desired, held in place by hand, a strap or other retention device. If an endotracheal tube is used, the interface 14 or portion of the interface 14 can be coupled to the endotracheal tube. In the illustrated arrangement, the nasal prongs can be coupled to the nasal mask or tube and the nasal prongs can be inserted into the nostrils of the infant patient 12. The nasal mask 14 can be held in place by any suitable retention mechanism, such as a chin strap or head strap.

Once the patient interface 14 is in place on the infant patient 12, the CPAP therapy can be commenced. A flow of breathing gas is supplied to the infant patient 12 by the patient interface 14 at the CPAP or PEEP level, as regulated by the expiratory pressure device 60. As discussed, preferably the expiratory pressure device 60 is configured to produce pressure oscillations within the system 10, which is believed to have an improved therapeutic effect on the infant patient 12. The CPAP therapy can continue for a desired period of time.

If necessary or desirable, resuscitation therapy can be administered. As described above, the occlusion valve 70 can be actuated to block the exit of expiratory gases from the system 10 and cause the pressure within the system 10 to rise toward or to the PIP pressure to deliver a resuscitation breath to the infant patient 12. The occlusion valve 70 can be moved to an open position, or allowed to return to an open position, to return the system to the PEEP. In some arrangements, the actuation of the occlusion valve 70 is accomplished manually. The actuation and release of the occlusion valve 70 can be repeated at a desired frequency, such as between about 40-60 breaths per minute, for a suitable duration, such as about 3-5 minutes. However, if necessary or desirable, the duration of the resuscitation therapy can be up to 15-30 minutes, or longer. At the conclusion of the resuscitation therapy, the system 10 can automatically return to the CPAP mode at the PEEP. Accordingly, with the illustrated system 10, resuscitation therapy can be immediately commenced on an infant patient 12 that is undergoing CPAP therapy without requiring the set-up of additional equipment and without requiring the replacement of the patient interface 14.

Figure 4:
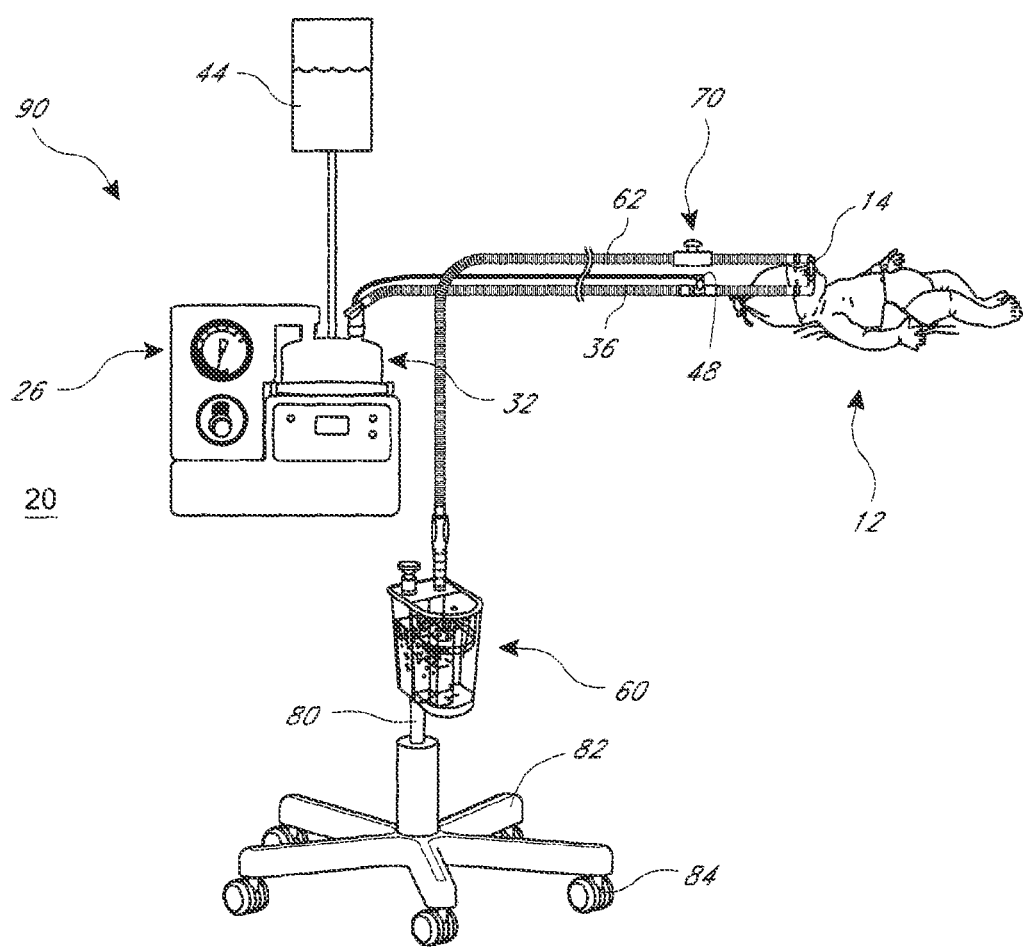
FIG. 4 is an illustration of a modification of the system of FIG. 1, in which the inspiratory pressure device is integrated with the humidifier.
Figure 5:
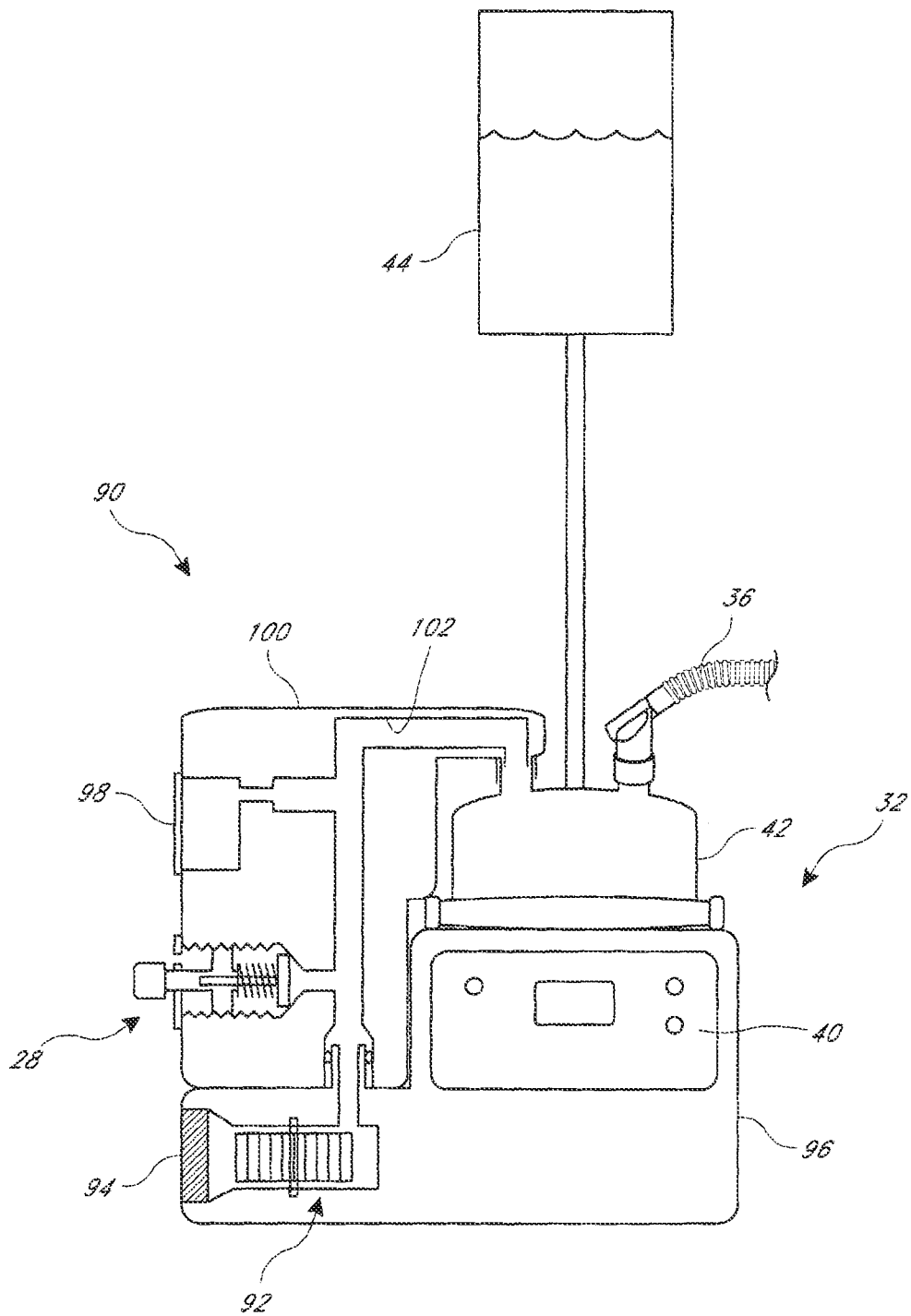
FIG. 5 is a partial sectional view of the integrated inspiratory pressure device and humidifier of FIG. 4.

FIGS. 4 and 5 illustrate a modification of the system 10 of FIG. 1. Because the system of FIGS. 4 and 5 is similar to the system 10 of FIG. 1 in many respects, the same reference numbers are used to indication the same or corresponding components. In the system of FIGS. 4 and 5, the resuscitator 26 (or other inspiratory pressure device) is integrated with the humidifier 32 in a resuscitator/humidifier unit 90 (hereinafter "integrated unit 90"). In addition, preferably, the source of breathing gas 20 is or includes ambient air from an environment adjacent the integrated unit 90. Therefore, the integrated unit 90 preferably comprises a flow generator or flow source, such as a fan, gas pump or blower 92 (FIG. 5), which generates a flow of air. In some embodiments, however, the integrated unit 90 can be connected to a source of breathing gas, such as a gas cylinder or a wall supply, instead of or in addition to the flow generator. In some arrangements, the system can utilize supplemental breathing gases (oxygen or other suitable respiratory gases) that are blended in combination with air. However, in many arrangements, only air is used and the source of breathing gas (reference number 20 in FIG. 1) can be omitted.

In the illustrated arrangement, the integrated unit 90 generates a flow of breathing gas (e.g., air) and outputs the flow of breathing gas at a controlled pressure greater than atmospheric pressure to the humidifier, which humidifies the flow of breathing gas. The flow of humidified breathing gas is delivered to the patient 12 via the supply tube 36 and patient interface 14. Exhaled and unused gases are delivered to the expiratory pressure device 60 via the expiratory hose 62. The expiratory pressure device 60 can provide a minimum pressure or minimum backpressure within the system and, in particular, at the patient interface 14 preferably to or near the PEEP pressure. The occlusion valve 70 can be used to block the flow of breathing gas such that the inspiratory pressure device 26 can increase the pressure in the system preferably to or near the set PIP level. The system of FIGS. 4 and 5 preferably operates in substantially the same manner as described above with respect to the system 10 of FIG. 1.

With reference to FIG. 5, in addition to the blower 92, the integrated unit 90 preferably includes a filter 94 upstream from the blower 92. The filter 94 is of a suitable arrangement to separate impurities or other undesirable elements from the ambient air that is used to generate the flow of air within the system. The filter 94 and the blower 92 preferably can be coupled to or contained within a housing 96 that contains portions of the humidifier 40 and supports the humidifier chamber 42. The pressure adjustment valve 28 and a manometer 98, or other pressure gauge or measurement device, can be coupled to or contained within a housing 100 that is separate from the housing 96. Preferably, the housing 100 can be removable from the housing 96. When the housing 100 is removed, the integrated unit 90 can be used as a blower 92 and humidification system 32 without the resuscitation feature. In the illustrated arrangement, the housing 100 defines or contains a conduit 102 for delivering the flow of breathing gas from the blower 92 to the humidification chamber 42 of the humidifier system 32. When the housing is removed, an auxiliary conduit (not shown) can be utilized in place of the conduit 102. Alternatively, an auxiliary conduit can be integrated with or otherwise incorporated with the housing 96 that is utilized when the housing 100 is removed. A valve arrangement could be configured to automatically switch between the conduit 102 and the auxiliary conduit depending on the presence or absence of the housing 100.

Figure 6:
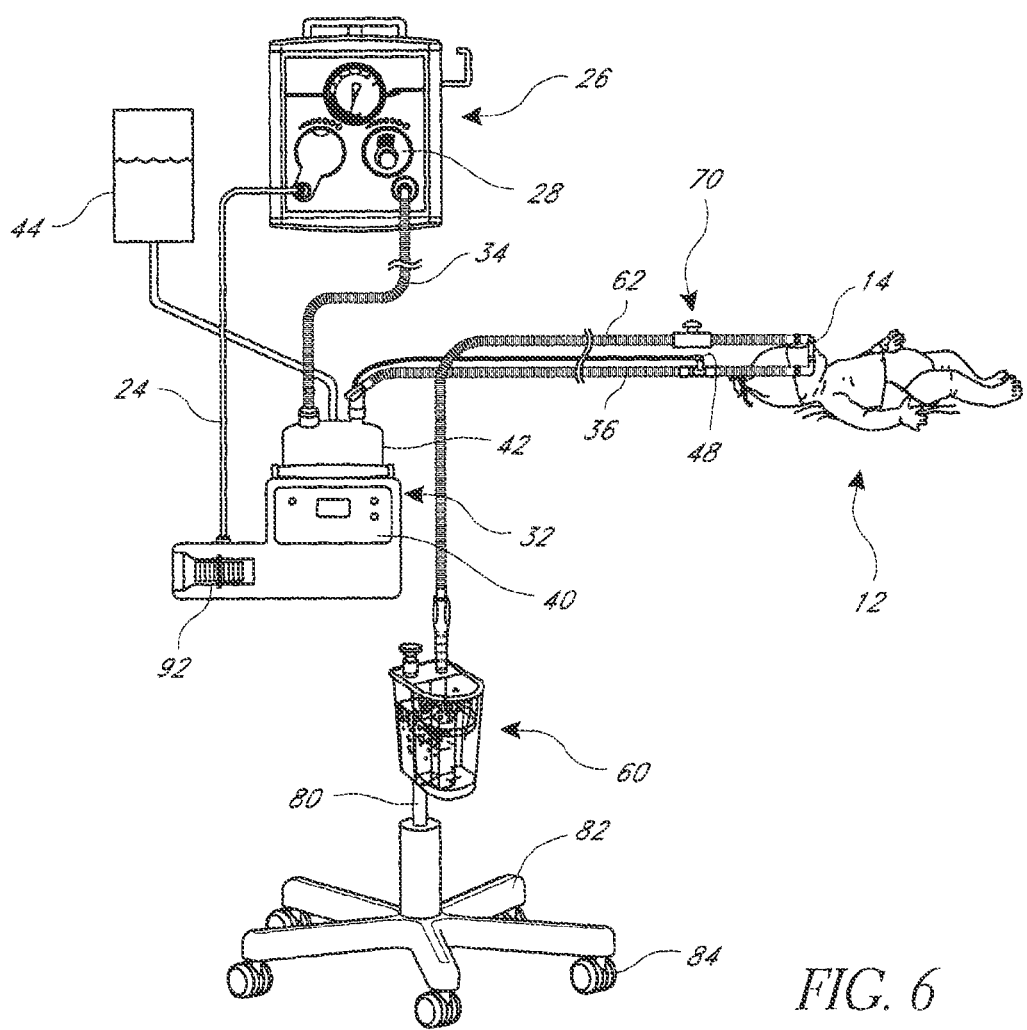
FIG. 6 is an illustration of another modification of the system of FIG. 1, in which a flow generator is integrated with the humidifier.

With reference to FIG. 6, in another modification of the systems of FIG. 1 and FIGS. 4 and 5, the flow generator (hereinafter "blower 92") is integrated with the humidifier 40 of the humidification system 32. However, unlike the system of FIGS. 4 and 5, the resuscitator 26 is a separate system component from the humidifier 40, humidification chamber 42 or the entire humidifier system 32. Thus, in the system of FIG. 6, the blower 92 is connected to the resuscitator 26 via the supply line 24 to deliver the flow of air (or other breathing gas) from the blower 92 to the resuscitator 26. The flow of air then flows from the resuscitator 26 to the humidification chamber 42 of the humidifier system 32 and to the patient 12 as described above. If the resuscitator 26 is not necessary or desired, the blower 92 can be connected to the humidification chamber 42 of the humidifier system 32, without passing through the resuscitator 26, via a suitable internal or external auxiliary conduit, as described above.

Although described in the context of an infant patient system, the illustrated system can be used in, or modified for use in, other applications or contexts, as well. Thus, although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In particular, the skilled artisan will appreciate, in view of the present disclosure, that certain advantages, features and aspects of the system may be realized in a variety of other applications, many of which have been noted above. Additionally, it is contemplated that various aspects and features of the invention described can be practiced separately, combined together, or substituted for one another, and that a variety of combination and subcombinations of the features and aspects can be made and still fall within the scope of the invention. Thus, it is intended that the scope of the present invention herein disclosed should not be limited by the particular disclosed embodiments described above, but should be determined only by a fair reading of the claims.

What is claimed is:

1. An infant resuscitation system configured for use on an infant patient, the infant resuscitation system comprising:
    a flow generator configured to generate a flow of breathing gas at a controlled pressure greater than atmospheric pressure, the flow generator configured to output the flow of breathing gas at at least a PEEP level and at a PIP level, the PIP level and the PEEP level being adjustable;
    a supply tube configured to receive the flow of breathing gas generated by the flow generator and to deliver the flow of breathing gas to the infant patient via a patient interface;
    an actuator positioned at the patient interface and moveable between a first position and a second position, the first position causing the flow generator to provide pressure at the PEEP level, and the second position causing the flow generator to raise the pressure to the PIP level to deliver a resuscitation breath to the infant patient; and
    wherein the actuator is configured to move between the first position and the second position in response to an external mechanical force.

2. The infant resuscitation system of claim 1, wherein the actuator is a push button arrangement.

3. The infant resuscitation system of claim 1, wherein the actuator is configured to be manually operated.

4. The infant resuscitation system of claim 1, wherein the actuator comprises a valve body movable between an open position and a closed position.

5. The infant resuscitation system of claim 1, wherein the actuator is used to cause the flow generator to provide repeated resuscitation breaths to the infant patient at the PIP level with intervening periods at the PEEP level.

6. The infant resuscitation system of claim 5, wherein the resuscitation breath delivered by the flow generator is at a rate of about 40-60 breaths per minute.

7. The infant resuscitation system of claim 5, wherein a relative duration of a resuscitation breath time at the PIP level to an exhalation time at the PEEP level is between 40:60 and 60:40.

8. The infant resuscitation system of claim 1, wherein the actuator is positioned at or on the patient interface.

9. The infant resuscitation system of claim 1, wherein the infant resuscitation system further comprises a pressure relief valve adjustable such that the PEEP level can be adjusted.

10. The infant resuscitation system of claim 9, wherein the PEEP level of the infant resuscitation system is regulated by the flow generator.

11. The infant resuscitation system of claim 9, wherein the PEEP level is adjustable within an adjustment range of about 5-70 cmH2O.

12. The infant resuscitation system of claim 1, wherein the infant resuscitation system further comprises an adjustment mechanism that allows the PIP level to be adjusted to a desired pressure level.

13. The infant resuscitation system of claim 1, wherein the flow generator comprises a fan or a blower that generates the flow of air.

14. The infant resuscitation system of claim 1, wherein the infant resuscitation system further comprises a source of gas and the flow generator is configured to receive gas from the source of gas.

15. The infant resuscitation system of claim 14, wherein the source of breathing gas is or includes ambient air from an environment adjacent the flow generator.

16. The infant resuscitation system of claim 15, wherein the source of breathing gas further comprises a gas cylinder or a wall supply.

17. The infant resuscitation system of claim 16, wherein the infant resuscitation system can utilize supplemental breathing gases from the gas cylinder or wall supply that are blended in combination with the ambient air.

18. The infant resuscitation system of claim 1, wherein the patient interface provides a sealed system that delivers the flow of breathing gas to the infant patient.

19. The infant resuscitation system of claim 1, wherein the infant resuscitation system is further configured to provide CPAP therapy.

20. The infant resuscitation system of claim 19, wherein one or more resuscitation breaths are provided through the patient interface used for the CPAP therapy without requiring removal of the patient interface from the infant patient.

21. The infant resuscitation system of claim 1, wherein the infant resuscitation system is capable of providing PAP or CPAP therapy to an infant patient for an extended period of time, while also permitting resuscitation breaths to be delivered to the infant patient if or when necessary.

22. The infant resuscitation system of claim 1, wherein the infant resuscitation system further comprises a humidifier integrated with the flow generator as a single unit, wherein the humidifier receives the flow of breathing gas from the flow generator, the humidifier humidifying the flow of breathing gas to create a flow of humidified breathing gas, and the supply tube receiving the flow of humidified breathing gas from the humidifier and delivering the flow of humidified breathing gas to the infant patient via the patient interface.

23. The infant resuscitation system of claim 22, wherein the supply tube is a heated supply tube such that a temperature of the flow of breathing gas is maintained at an elevated level within the supply tube to avoid or limit condensation within the supply tube or the patient interface.

24. The infant resuscitation system of claim 23, wherein a sensor or a probe is configured to be coupled to the humidifier and the supply tube to detect the temperature and/or a flow rate of the flow of breathing gas through the supply tube.

25. The infant resuscitation system of claim 24, wherein the humidifier utilizes information from the sensor or the probe to control at least one operating parameter of the humidifier to maintain the temperature and/or a humidity of the flow of humidified breathing gas within the supply tube within a desired range or at a desired level.

26. The infant resuscitation system of claim 22, wherein the humidifier comprises a humidifier heater and a humidity chamber, the humidity chamber holds a volume of liquid which is heated by the humidifier to create a vapor within the humidity chamber that is transferred to the flow of breathing gas.

27. The infant resuscitation system of claim 26, wherein the humidifier can be adjusted to a desired temperature and absolute humidity.

28. The infant resuscitation system of claim 22, wherein the infant resuscitation system further comprises an expiratory pressure device, wherein gases flow from the patient interface to the expiratory pressure device through an expiratory limb, and the flow of humidified gases is provided to the infant patient through the supply tube.

29. The infant resuscitation system of claim 28, wherein the expiratory pressure device is configured to provide a minimum pressure or minimum backpressure within the infant resuscitation system at the patient interface, which can be referred to as a PEEP.

30. The infant resuscitation system of claim 28, wherein the expiratory pressure device is a bubbler.

* * * * *